United States Patent [19]

Ferreira et al.

[11] Patent Number: 5,580,855
[45] Date of Patent: *Dec. 3, 1996

[54] PEPTIDES

[75] Inventors: Sergio H. Ferreira, Est. Sao Paulo, Brazil; Adrian F. Bristow, Hertfordshire; Stephen Poole, London, both of England

[73] Assignee: British Technology Group Limited, London, England

[*] Notice: The term of this patent shall not extend beyond the expiration date of Pat. No. 5,389,615.

[21] Appl. No.: 330,845

[22] Filed: Oct. 27, 1994

Related U.S. Application Data

[63] Continuation of Ser. No. 95,856, Jul. 23, 1993, Pat. No. 5,389,615, which is a continuation of Ser. No. 438,404, Dec. 20, 1989, abandoned.

[30] Foreign Application Priority Data

Mar. 28, 1988 [GB] United Kingdom ............ 8807427
Dec. 9, 1988 [GB] United Kingdom ............ 8828833

[51] Int. Cl.$^6$ .................. A61K 38/00; C07K 5/00; C07K 5/08
[52] U.S. Cl. ........................ 514/18; 530/331
[58] Field of Search ................. 530/331; 514/18

[56] References Cited

U.S. PATENT DOCUMENTS

| | | |
|---|---|---|
| 3,778,426 | 11/1973 | Najjar . |
| 4,127,534 | 11/1979 | Coy et al. . |
| 4,505,853 | 3/1985 | Goldstein et al. . |
| 4,855,407 | 9/1989 | Wang ........................ 530/334 |
| 5,013,723 | 5/1991 | Sisto et al. . |
| 5,028,592 | 7/1991 | Lipton et al. . |
| 5,389,615 | 2/1995 | Ferreira et al. ............... 530/331 |

FOREIGN PATENT DOCUMENTS

| | | |
|---|---|---|
| 0026640 | 4/1981 | European Pat. Off. . |
| 0099286 | 1/1984 | European Pat. Off. . |
| 2118134 | 7/1972 | France . |
| 2529461 | 6/1984 | France . |
| 53-101365 | 9/1978 | Japan . |
| 2058085 | 4/1981 | United Kingdom . |
| 2163166 | 2/1986 | United Kingdom . |
| 8002141 | 10/1980 | WIPO . |
| 8400108 | 1/1984 | WIPO . |
| 8604334 | 7/1986 | WIPO . |

OTHER PUBLICATIONS

"Nomenclature and Symbolism for Amino Acids and Peptides", Europ. Jour. of Biochemistry 138, pp. 9–37.

Ferreira et al "Central and Peripheral Antialgesic Action of Aspirin . . . ", Europ. Jour. of Pharmacology, 58 (1978) pp. 39–48.

Smolders et al "Conformational Study by $^{13}$C nuclear Magnetic . . . ", Canadian Jour. of Biochemistry, vol. 58, No. 11 Nov. 1980.

Moncada et al "Pain and Inflammatory Mediators", Handbook of Exp. Pharmacology, vol. 150/61 1978.

Gorne et al "Action of Substance P and Substance P fragments . . . ", Pharmazie, 37, H.4 (1982).

Scientific American, vol. 253 Oct. 1985, p. 96.

Ferreira et al, Nature vol. 334, No. 6184 pp. 698–700 (Aug. 25, 1988).

Fujino et al, Chemical Abstracts 90, 104363v (1979).

Auriault et al, FEBS Letters 153 1, pp. 11–15 (Mar. 1983).

Nicolaides et al, Int. J. Peptide Protein Res. 25 (1985) pp. 435–441.

Furuta et al, J. Pharmacol. 83(1), pp. 43–88 (1984).

Herman et al, Naturwissenschaften 72(2) pp. 85–86 (1985).

Goerne et al, Pharmazie 37(4) 299–300 (1982).

Eberle, A. N. (ed) "The Melanotropins, chemistry . . . ", Karger Press, 1988, pp. 336–337 and 346–348.

Hiltz, M. E. et al, "Anti–inflammatory activity of . . . ", Pergamon Press, USA, vol. 12, pp. 767–771.

Lipton, J. M. & Catania, A. "α–MSH peptides modulate . . . ", Pergamon Press, USA, 1992, pp. 123–136.

McLaughlin, C. L. et al "Food intake and body temperature . . . " Physiology & Behavior, Pergamon Press, USA, vol. 52 (1992), pp. 1155–1160.

Chemical Abstracts #111:73430a, vol. 111, 1989.

Richards et al. "Effect of a α–MSH 11–13 (Lysine–Proline–Valine)", Peptides (1984) pp. 815–817, vol. 5.

Dryland et al "Peptide Synthesis 8." Perkin Transaction 1, 125, 1986.

R. Coomans et al "Antalgic properties of peptides . . . ", Eur. J. Med. Chem—Chimica Therapeutica Jul.–Aug. 1977–12 No. 4.

R. Coomans et al "Pharmacological study and synthesis of peptide . . . " L'Ingineur Chimiste (Brussels) 59 (284–285) 48–66 (1977).

Primary Examiner—Elizabeth C. Weimar
Assistant Examiner—S. G. Marshall
Attorney, Agent, or Firm—Nixon & Vanderhye

[57] ABSTRACT

Peptides, the C-terminal amides thereof and the pharmaceutically acceptable salts of the said peptides and amides are useful in the prevention and treatment of pain.

7 Claims, 9 Drawing Sheets

PEPTIDES

This is a Rule 60 of application Ser. No. 08/095,856, filed Jul. 23, 1993, now U.S. Pat. No. 5,389,615, which is a continuation of Ser. No. 07/438,404, filed Dec. 20, 1989 now abandoned.

The present invention relates to peptides, to their preparation and to their use.

The term Interleukin-1 (IL-1) describes two pluri-potent inflammatory proteins produced by activated macrophages and other cell types. Two genes encode the two forms of IL-1, IL-1α and IL-1β, which have amino acid sequences with only 26% homology. Nevertheless, IL-1α and IL-1β are reported to have similar biological activities with few exceptions. Indeed both molecules appear to act at the same receptor. There is good evidence that both have a role as a haemopoietic growth factor and in the pathology of a number of inflammatory diseases. Also, IL-1 has anti-tumor activity.

Since IL-1 releases prostaglandins, which sensitise pain receptors in man and in experimental animals, IL-1α and IL-1β were tested for hyperalgesic activity. It was found that IL-1β is an extremely potent hyperalgesic agent with about three thousand times the activity of IL-1α. Further, a family of peptides has been discovered which very effectively antagonise hyperalgesia induced by IL-1β and by other inflammatory agents. These peptides may therefore be used as analgesics.

Accordingly, the present invention provides the use, in the preparation of a medicament for use in the prevention or treatment of pain, of a peptide of formula (I):

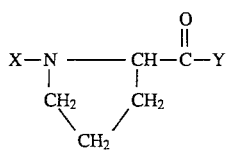

wherein X is

H$_2$N—[CH$_2$]$_4$—CH(NH$_2$)—C(=O)— or

H$_2$N—C(=NH)—NH—[CH$_2$]$_3$—CH(NH$_2$)—C(=O)—, and Y is a hydroxy group or an amino acid residue; excluding Lys-Pro-Arg, Arg-Pro-Tyr, Arg-Pro and Lys-Pro. The peptide of formula (I) may be in the form of its C-terminal amide. A pharmaceutically acceptable salt of the peptide of formula (I) or its C-terminal amide may be used.

An article by D. B. Richards and J. M. Lipton in Peptides 5 (1984) 815–817 discloses the antipyretic effect of the tripeptide Lys-Pro-Val in febrile rabbits. Some other peptides of formula (I) are known but some are novel. Accordingly, the present invention provides a peptide of formula (I), C-terminal amide or pharmaceutically acceptable salt as defined above, with the further proviso that the peptide of formula (I) is not:

(i) a peptide of formula (III):

wherein Y$^1$ is Val, Phe, Pro, Gly, Thr, Lys or Glu;

(ii) a peptide of formula (IV):

wherein Y$^2$ is Val, Phe, D-Pro, Pro, Gln, Gly, Lys, Arg or Glu; or (iii) Arg-D-Pro-Pro, Arg-D-Pro-Lys, D-Lys-Pro or Arg-D, L-Pro.

The invention also provides a process for the preparation of the novel peptides of formula (I), their C-terminal amides and the pharmaceutically acceptable salts of these peptides and amides, which process comprises chemically synthesising a said peptide, optionally as a C-terminal amide, and, if desired, converting the resulting compound into a pharmaceutically acceptable salt thereof.

Each of the constituent amino acid residues of the peptide of formula (I) which is chiral may be present as either the D or the L optical isomer. The D isomer is particularly preferred in the case of the central proline residue. Using the three letter system of denoting amino acids, in which the symbols denote the L configuration of the chiral amino acid unless otherwise stated, X may be Lys, D-Lys, Arg or D-Arg. Indeed a peptide of formula (I) may be present as a racemic mixture or as an optically pure isomer. Preferably X is Lys or D-Lys.

When Y is a hydroxy group the peptide of formula (I) is a dipeptide. However, tripeptides are preferred. Y is typically an α-amino acid residue. More particularly Y is generally a naturally occurring amino acid residue.

Preferably Y is a neutral amino acid residue. An aliphatic amino acid residue is preferred to an aromatic amino acid residue and a neutral amino acid residue to an acidic amino acid residue. In particular Y may be a threonine or valine residue. When Y is a threonine residue, one embodiment of the peptide of formula (I) is a peptide of the following formula (II):

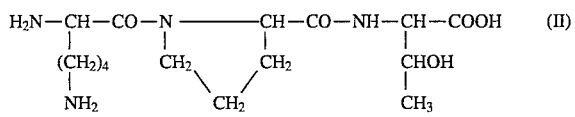

Y may also be a residue derived from glycine. Y may be an alanine or serine residue or, preferably, a leucine or isoleucine residue. Y may also suitably be an acidic amino acid residue. Y is then typically a residue of aspartic acid or asparagine.

Especially preferred peptides of formula (I) are Lys-Pro-Thr, Lys-D-Pro-Thr, Lys-Pro-Val and Lys-D-Pro-Val. Also preferred are D-Lys-Pro-Thr, Arg-Pro-Val, D-Arg-Pro-Val, Arg-D-Pro-Val; D-Arg-D-Pro-Val, Arg-Pro-Thr, D-Arg-Pro-Thr, Arg-D-Pro-Thr and D-Arg-D-Pro-Thr. A dipeptide may be Lys-D-Pro or Arg-D-Pro.

The peptides of formula (I), both new and old, can be prepared by chemical synthesis. A peptide is built up by condensation of the constituent amino acids in the order in which they occur in formula (I). The peptide may be obtained with a free carboxy or amide (—CONH$_2$) group at its C-terminus. Solid-phase or solution methods may be employed. The resultant peptide may be converted into a pharmaceutically acceptable salt if desired.

In solid-phase synthesis, the amino acid sequence of formula (I) is built up sequentially from the C-terminal amino acid which is bound to an insoluble resin. When the desired peptide has been produced, it is cleaved from the resin. When solution-phase synthesis is employed, the peptide may again be built up from the C-terminal amino acid. The carboxy group of this acid remains blocked throughout by a suitable protecting group, which is removed at the end of the synthesis.

Whichever technique, solid-phase or solution-phase, is employed each amino acid added to the reaction system typically has a protected amino group and an activated carboxy group. An amino group may be protected by the fluoren-9-ylmethoxycarbonyl (Fmoc) or t-butoxycarbonyl (Boc) group. A carboxy group may be activated as a pentafluorophenyl or 1-oxo-2-hydroxy-dihydrobenzotriazine ester. Each condensation step may be effected in the presence of dicyclohexylcarbodiimide or 1-hydroxybenzotriazole. The side chain amino group of lysine and the side chain hydroxy group of threonine may be protected, as their butyl ethers (in the case of serine and threonine), butyl esters (in the case of aspartic acid), butyloxycarbonyl derivative (lysine), and 4,4'-dimethoxybenzhydryl group (asparagine). After each step in the synthesis, the α-amino protecting group is removed. Any side-chain protecting groups are generally removed at the end of the synthesis.

The peptides may be prepared with either a C-terminal carboxy or a C-terminal amide group. In solid phase peptide synthesis, this may be determined by how the C-terminal amino acid is linked to the resin support and/or how the final peptide is cleaved from the resin support. Typically the resin is a styrene and/or divinylbenzene polymer. The C-terminal amino acid may be linked to the resin via an ester linkage which can be cleaved by a strong acid such as HBr in trifluoroacetic acid or HF to give the peptide with a C-terminal carboxy group. Ammonolysis can give the corresponding amide instead.

An alternative method of obtaining a peptide amide by solid phase synthesis is to arrange for the C-terminal amino acid of the peptide to be linked to the resin via a peptide aminobenzhydryl bond. This can be formed by coupling with dicyclohexylcarbodiimide and can be cleaved with HF, typically in the cold. For solution phase synthesis, whether a C-terminal carboxy or amide group is present may depend upon how the carboxy group of the C-terminal amino acid is blocked and, at the end of the synthesis, unblocked. A peptide with a C-terminal carboxy group can be converted into one with a C-terminal amide group and vice versa.

The resultant peptide may be converted into a pharmaceutically acceptable salt. It may be converted into an acid addition salt with an organic or inorganic acid. Suitable acids include acetic, succinic and hydrochloric acid. Alternatively, the peptide may be converted into a carboxylic acid salt such as the ammonium salt or an alkaline metal salt such as the sodium or potassium salt.

The peptides of formula (I) and their amides and salts are analgesics. Pain may therefore be treated or prevented in a human or animal by administration of an effective amount of a peptide of formula (I) or C-terminal amide or pharmaceutically acceptable salt thereof. Pain can therefore be alleviated.

Accordingly, the present invention provides a peptide of formula (I):

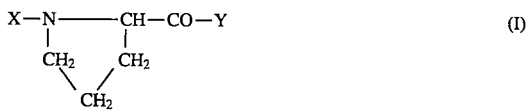

wherein X is

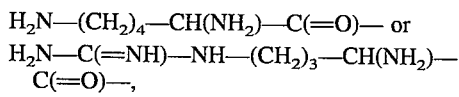

and Y is a hydroxy group or an amino acid residue, excluding Lys-Pro-Arg, Arg-Pro-Tyr, Arg-Pro and Lys-Pro; the C-terminal amide of a said peptide of formula (I); and pharmaceutically acceptable salts of a said peptide of formula (I) and the C-terminal amide thereof; for use as an analgesic.

One of the preferred tripeptides of the invention, Lys-Pro-Thr, forms part of the sequence of Il-1β. Both it and its D-Pro racemate antagonise hyperalgesia evoked by Il-1β. However, the all n compound has also been found to act as an agonist at certain concentrations; doses in rats of >50 μg/150 g rat evoke hyperalgesia. The D-Pro compound did not exhibit this agonist activity and is therefore preferable to the all n compound even though its analgesic activity is less than that of the L compound. The $ED_{50}$ values in rats of Lys-Pro-Thr and Lys-D-Pro-Thr have been calculated as approximately 25 and 85 μg/150 g rat respectively. It has further been found that the tripeptides Lys-Pro-Val and Lys-D-Pro-Val are more potent antagonists of Il-1β-evoked hyperalgesia than Lys-D-Pro-Thr.

Additional evidence of the more potent antagonist activity of the tripeptides having a C-terminal valine residue, compared to those having a C-terminal threonine residue, comes from the fact that both Lys-Pro-Val and Lys-D-Pro-Val antagonise hyperalgesia evoked by $PGE_2$. This activity is not exhibited by Lys-Pro-Thr or-Lys-D-Pro-Thr. Lys-Pro-Val and its D-Pro racemate in fact antagonise $PGE_2$ evoked hyperalgesia at higher dosage levels than those at which they antagonise Il-1β evoked hyperalgesia. The $ED_{50}$ values in rats are approximately 170 μg/150 g rat and 140 μg/150 g rat respectively for Lys-Pro-Val and Lys-D-Pro-Val antagonising $PGE_2$ evoked hyperalgesia. For Il-1β evoked hyperalgesia the relevant $ED_{50}$ values are 70 μg/150 g rat and 40 μg/150 g rat respectively.

None of the tripeptides of the present invention are antagonists to hyperalgesia evoked by dibutryl cyclic adenosine monophosphate (DbcAMP). The lack of any such effect contrasts strongly with morphine, which is an effective antagonist to hyperalgesia evoked by DbcAMP. This therefore provides one indication that the peptides of formula (I) are not morphine-like in their activity.

An advantage of the peptides Lys-Pro-Thr and Lys-D-Pro-Thr is that, unlike both steroidal and non-steroidal (aspirin-like) analgesic drugs, as mentioned above they do not inhibit prostaglandin production which has a protective role in the stomach. Steroidal and non-steroidal (aspirin-like) drugs cause gastric lesions which limit their usefulness, particularly in the treatment of symptoms of rheumatoid arthritis for which IL-1β may in part be responsible. This problem of gastric lesions can therefore be obviated by use of the peptides of formula (I) and its salts.

A peptide of formula (I) and its C-terminal amide and salts may be given orally or parenterally, for example subcutaneously, intravenously, intramuscularly, intraperitoneally, intranasal or by buccal administration. Typically, a compound is administered to a human or animal in an amount of from 0.2 to 2 mg/kg per dose by either the oral route or a parenteral route.

For use, a peptide of formula (I) or a C-terminal amide or salt thereof is generally formulated with a pharmaceutically acceptable carrier or diluent. Conventional formulations, carriers, adjuvants and diluents may be employed. These will generally be determined by the route of administration.

The following Examples 1 to 19 illustrate the invention. A Reference Example showing that IL-1β is a potent hyperalgesic agent is also provided. In the Figures referred to in the Examples and the Reference Example:

Figure 6:
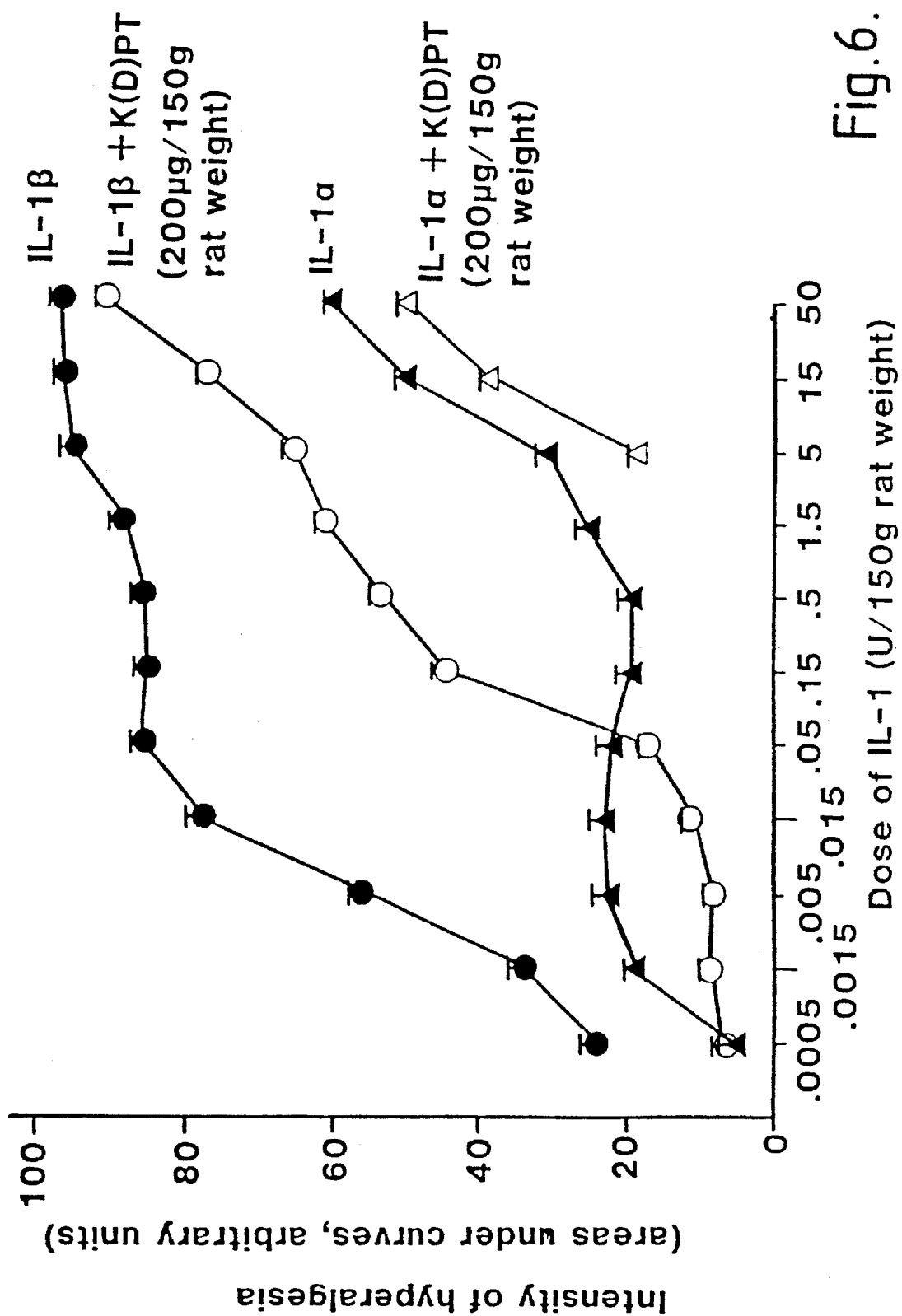
Figure 8:
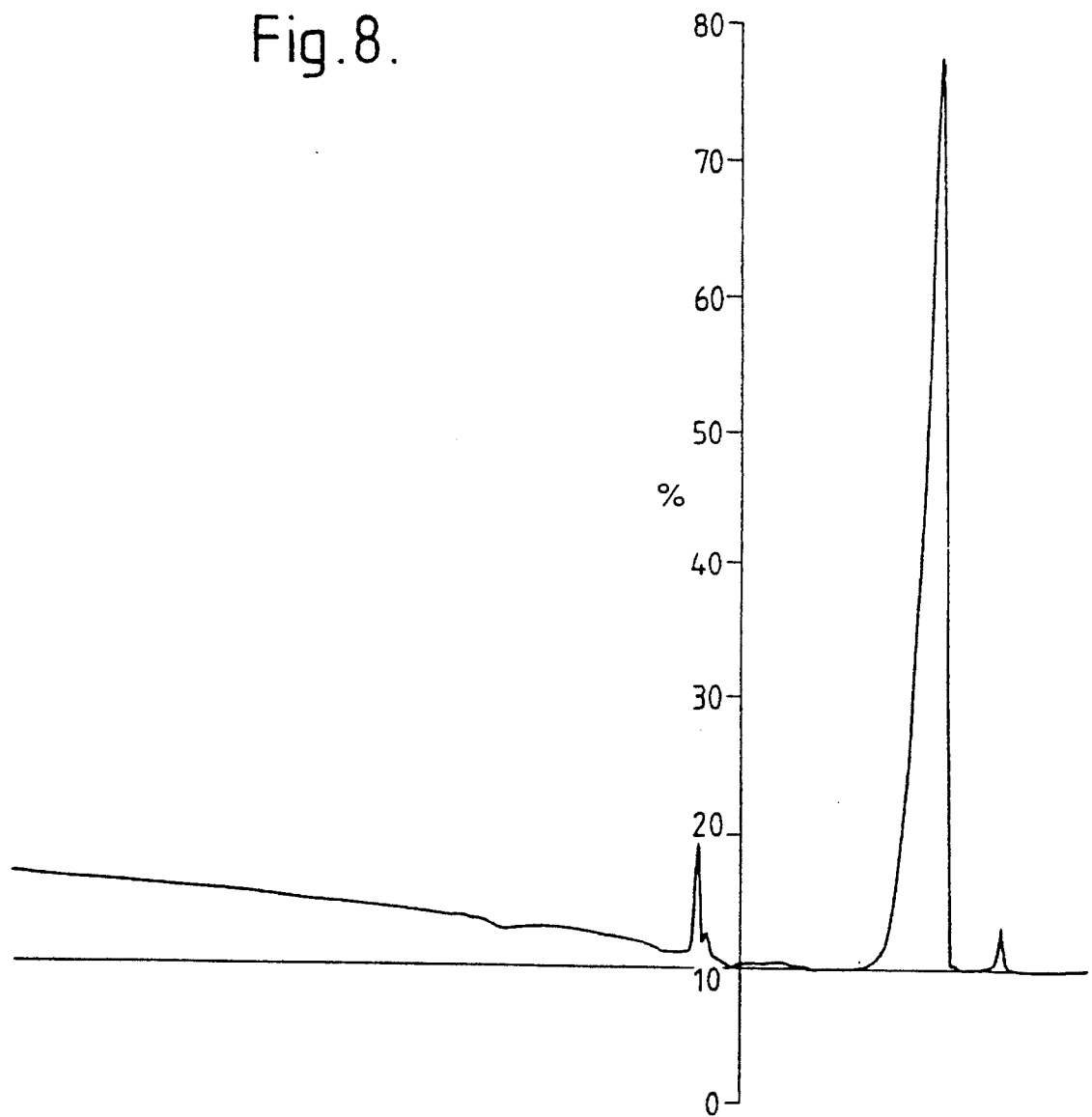

FIGS. 4a, b, and c shows the hyperalgesic effect of IL-1β and its attenuation by pretreatment with indomethacin (Reference Example);

FIGS. 5a and b shows the effect of three peptides on hyperalgesia evoked by IL-1β (Example 6);

FIG. 6 shows the hyperalgesic responses to IL-1α and IL-1β and the effect of peptide K(D)PT on those responses (Example 7);

FIGS. 7a, b, and c shows the effect of K(D)PT on the hyperalgesia evoked by $PGE_2$, carrageenan and IL-1β (Example 8);

FIG. 8 shows the HPLC trace of the peptide of Example 16; and

Figure 9:
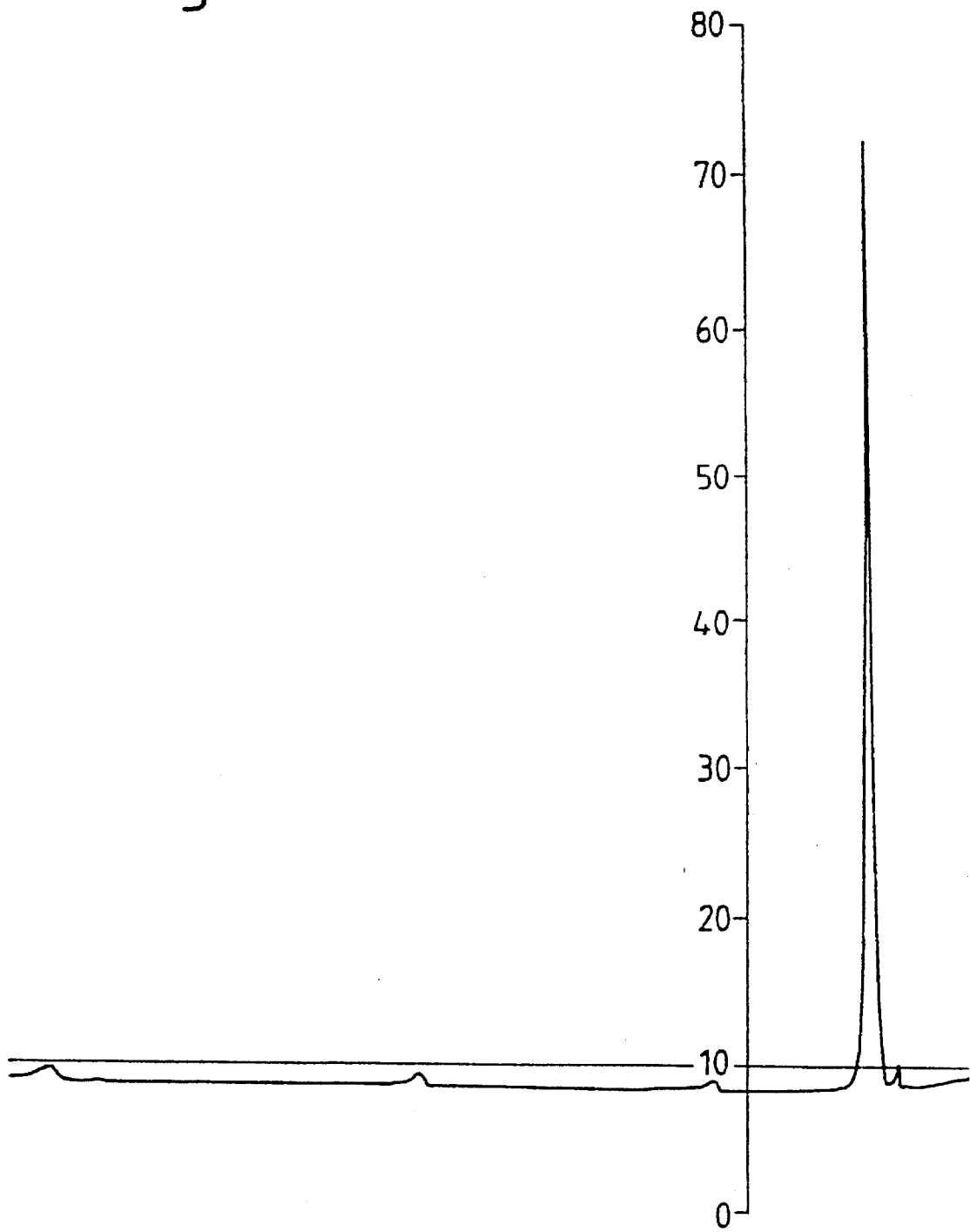

FIG. 9 shows the HPLC trace of the peptide of Example 17.

EXAMPLE 1

Preparation of Lys-Pro-Thr

The tripeptide Lys-Pro-Thr was synthesised using the Fmoc-polyamide method of solid-phase peptide synthesis (Dryland and Sheppard, Peptide Synthesis 8 "A system for solid phase synthesis under low pressure continuous flow conditions" J. Chem. Soc. Perkin. Trans. 1, 125, 1986). The solid phase support was a polydimethylacrylamide polymer constituted from the three monomers dimethylacrylamide (backbone monomer), bis-acryloyl-ethylene diamine (cross-linker) and acryloylsarcosamine methyl ester, (functionalising agent). The peptide to resin clearable linked agent used was the acid labile 4-hydroxymethyl-phenoxyacetic acid derivative.

All amino acid derivatives were added as their preformed symmetrical anhydride derivatives. Temporary Nα-amino group protection was afforded by the Fmoc group. Repetitive cleavage of this group was effected using 20% piperidine in N,N-dimethylformamide. Side-chain functionalities were protected as the butyl ester (threonine) and butyloxycarbonyl derivative (lysine).

After completion of the synthesis, the resultant peptide was cleaved from the resin support with 95% trifluoroacetic acid (TFA) containing a 5% scavenger mix. The peptide was purified by HPLC. Purity was established by camino acid analysis and by Fast Atom Bombardment Mass Spectrometry (FAB-MS):

| amino acid analysis | calculated | found | |
|---|---|---|---|
| | 1 | 1.00 | Lys |
| | 1 | 0.95 | Pro |
| | 1 | 0.98 | Thr |

FAB-MS: positive ion spectrum gave M+H$^+$ at m/z 345 (molecular weight is 344.415 (344)).

The purity was >80%. Purification to >95% was carried out by reverse-phase HPLC using a Hypersil (Trade Mark) WP 300 Butyl Column (150×4.6 mm). The buffers were: A=0.25% TFA and B=0.25% TFA is $CH_3CN$. Detection was by UV at 225 mm and the preparative load was 0.5 mg.

EXAMPLE 2

Preparation of Lys-D-Pro-Thr (1)

The tripeptide Lys-D-Pro-Thr was synthesised and purified in accordance with the procedure described in Example 1. Purity was established by amino acid analysis, FAB-MS and HPLC:

| amino acid analysis | calculated | found | |
|---|---|---|---|
| | 1 | 1.03 | Lys |
| | 1 | 1.05 | Pro |
| | 1 | 0.91 | Thr |

FAB-MS: positive ion spectrum gave M+H$^+$ at m/z 345 (molecular weight is 344.415 (344))

HPLC: column: μBondapak $C_{18}$ 3.8 mm×30 cm solvent: linear gradient 5–95% B over 20 minutes;

A=0.1% $TFA/H_2O$ and B=0.1% $TFA/CH_3CN$; flow rate 1.5 cm$^3$ min$^{-1}$ detection: Uv at 230 nm.

The purity was >80%. This was increased to >95% as described in Example 1.

EXAMPLE 3

Preparation of Lys-D-Pro-Thr (2)

The tripeptide Lys-D-Pro-Thr was also prepared by solid-phase synthesis using the Boc amino-protecting group. The starting resin was Boc-Thr-(benzyl(Bzl))-O-Resin. On deprotection with 20% TFA/DCM (DCM=dichloromethane) followed by neutralisation with 10% triethylamine the Boc-D-Pro was coupled using DCC (DCC=dicyclohexylurea)/DCM. Successful coupling was ascertained via the Kaiser test. Following deprotection and neutralisation of the Boc-D-Pro residue the final residue was coupled as the Boc-Lys-(benzyloxycarbonyl(Z)) derivative to give the peptide resin.

The peptide resin was subjected to HF cleavage at 0° C. for 45 minutes to give the crude peptide. Anisole was used as a scavanger during the cleavage. The crude peptide was purified on "Kieselgel 60" silica using a mobile phase of butanol: pyridine: acetic acid: $H_2O$ (B:P:A:W) of 90:90:18:72. After removal of the solvent in vacuo the sample was lyophilised from water to yield the pure peptide.

| amino acid analysis | calculated | found | |
|---|---|---|---|
| | 1 | 1.04 | Lys |
| | 1 | 0.95 | Pro |
| | 1 | 0.89 | Thr | thin layer chromatography:

1. B:P:A:W at 60:20:6:24 gave a single spot, ninhydrin positive, $R_f$ 0.21

2. B:A:W at 3:1:1 gave a single spot, ninhydrin positive, $R_f$ 0.24.

Figure 1:
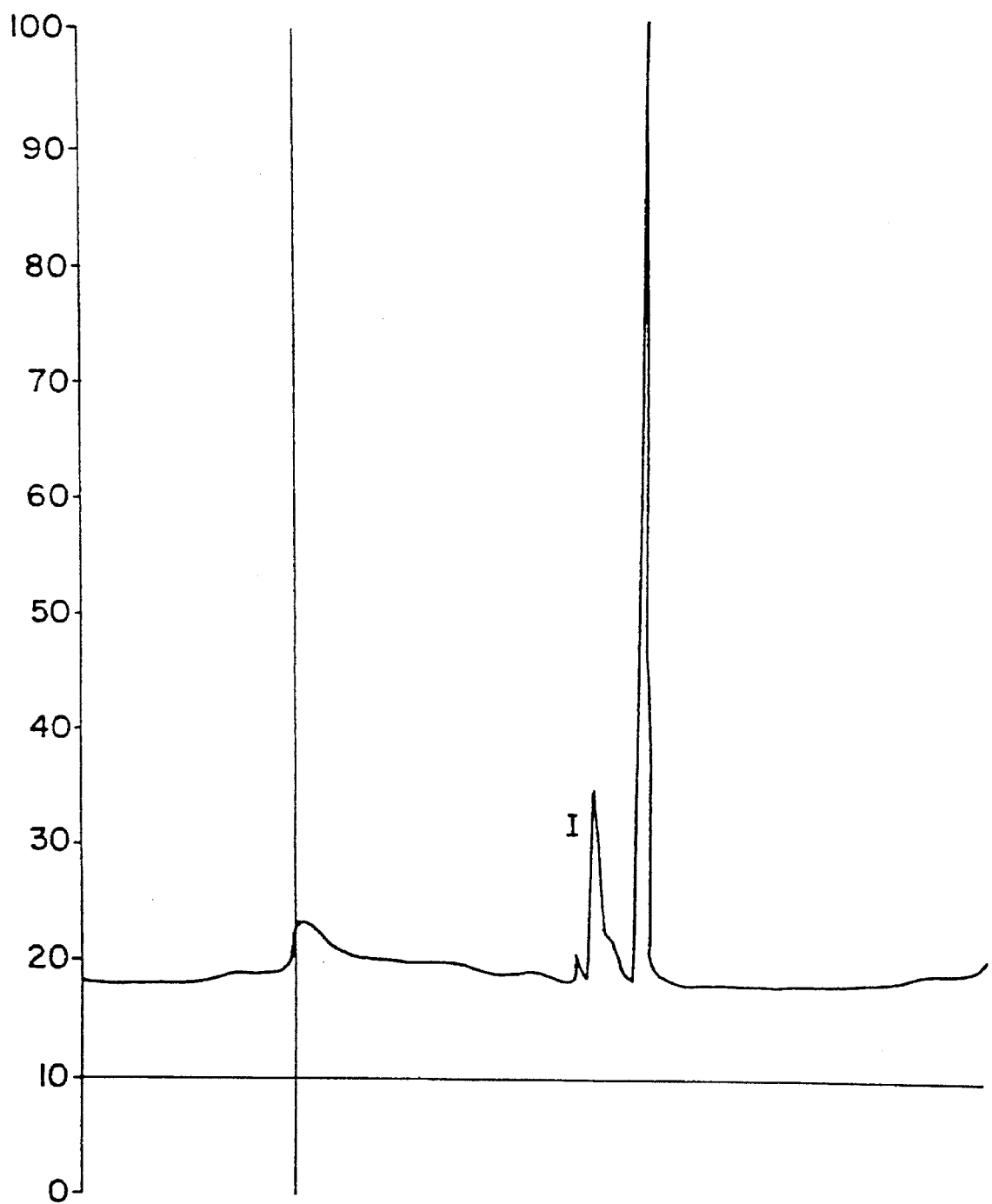
FIG. 1 shows the High Performance Liquid Chromatography (HPLC) trace of the purified peptide Lys-D-Pro-Thr (Example 3)

HPLC: The trace obtained is shown in FIG. 1 in which I denotes the solvent front. HPLC mode: Gilson. Column: Vydac C.18. Solvents: A 0.05M $NaH_2PO_4$ and B 60% $CH_3CN$ in A. Gradient: linear 0 to 100% B in 40 minutes. Recorder: 2 mm/min. Detector: 210 mm AUFS.

EXAMPLE 4

Preparation of Lys-Pro-Val

The tripeptide Lys-Pro-Val (KPV) was synthesised and purified in accordance with the procedure described in Example 1.

Purity was established by amino acid analysis and HPLC:

| Amino Acid Analysis | Lys | Pro | Val |
| --- | --- | --- | --- |
| Calculated: | 1.00 | 1.00 | 1.00 |
| Found: | 0.87 | 1.15 | 0.98 |

HPLC

Figure 2:
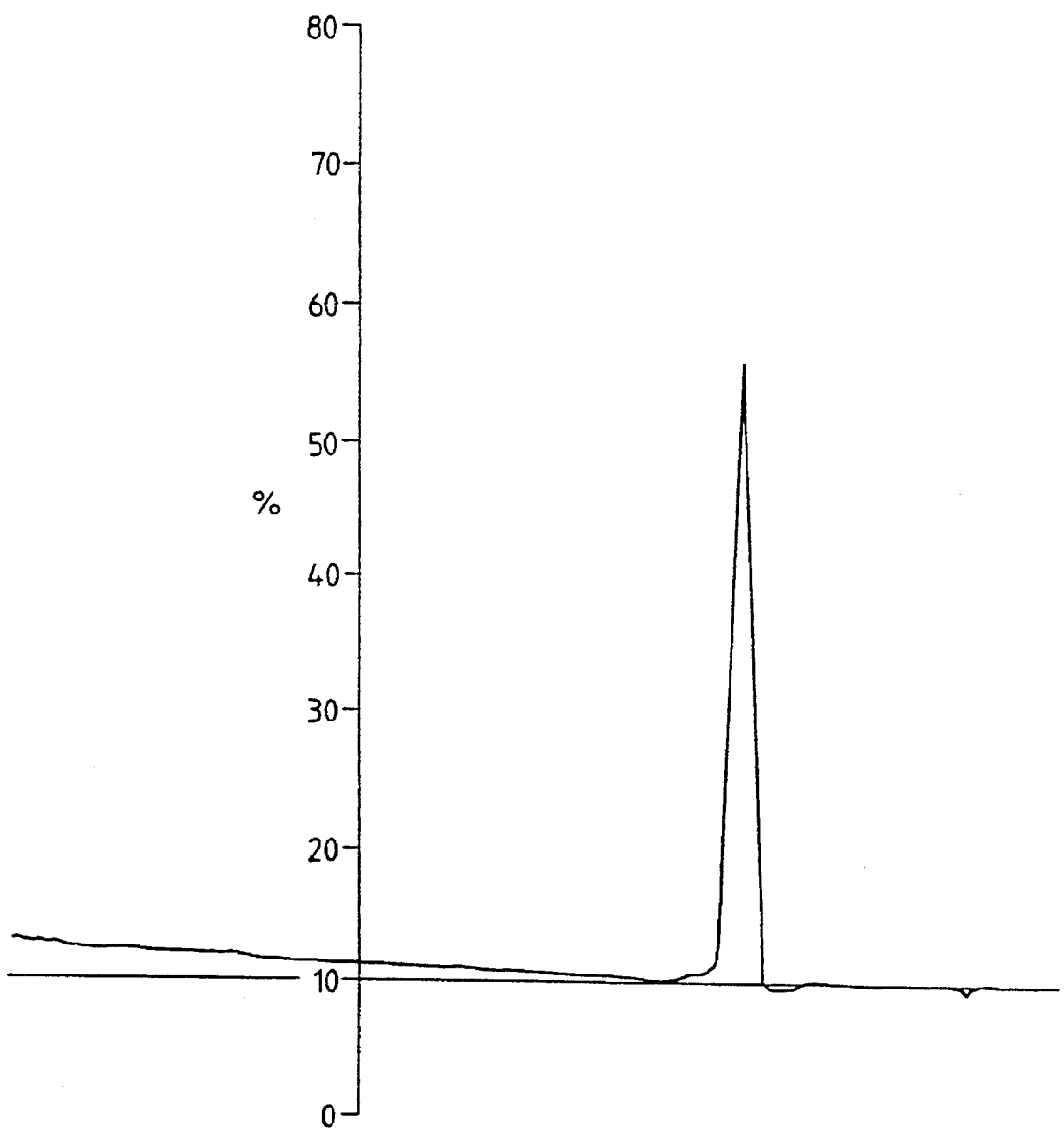
FIG. 2 shows the HPLC trace of purified KPV (Example 4)

The HPLC trace of the purified tripeptide is shown in FIG. 2.

Column: Vydac $C_{18}$ 4.6 mm×25 cm
Solvent: Linear gradient 0–30% B over 30 mins
Flow rate: 1.5 $cm^3$ $min^{-1}$
A=0.1% TFA/$H_2O$
B=0.1% TFA/$CH_3$ CN
Detection: UV at 230 nm.

EXAMPLE 5

Preparation of Lys-D-Pro-Val

This tripeptide was synthesised and purified as described in Example 4. Analysis results are as follows:

| Amino Acid Analysis | Lys | Pro | Val |
| --- | --- | --- | --- |
| Calculated: | 1.00 | 1.00 | 1.00 |
| Found: | 1.25 | 1.00 | 0.75 |

HPLC

Figure 3:
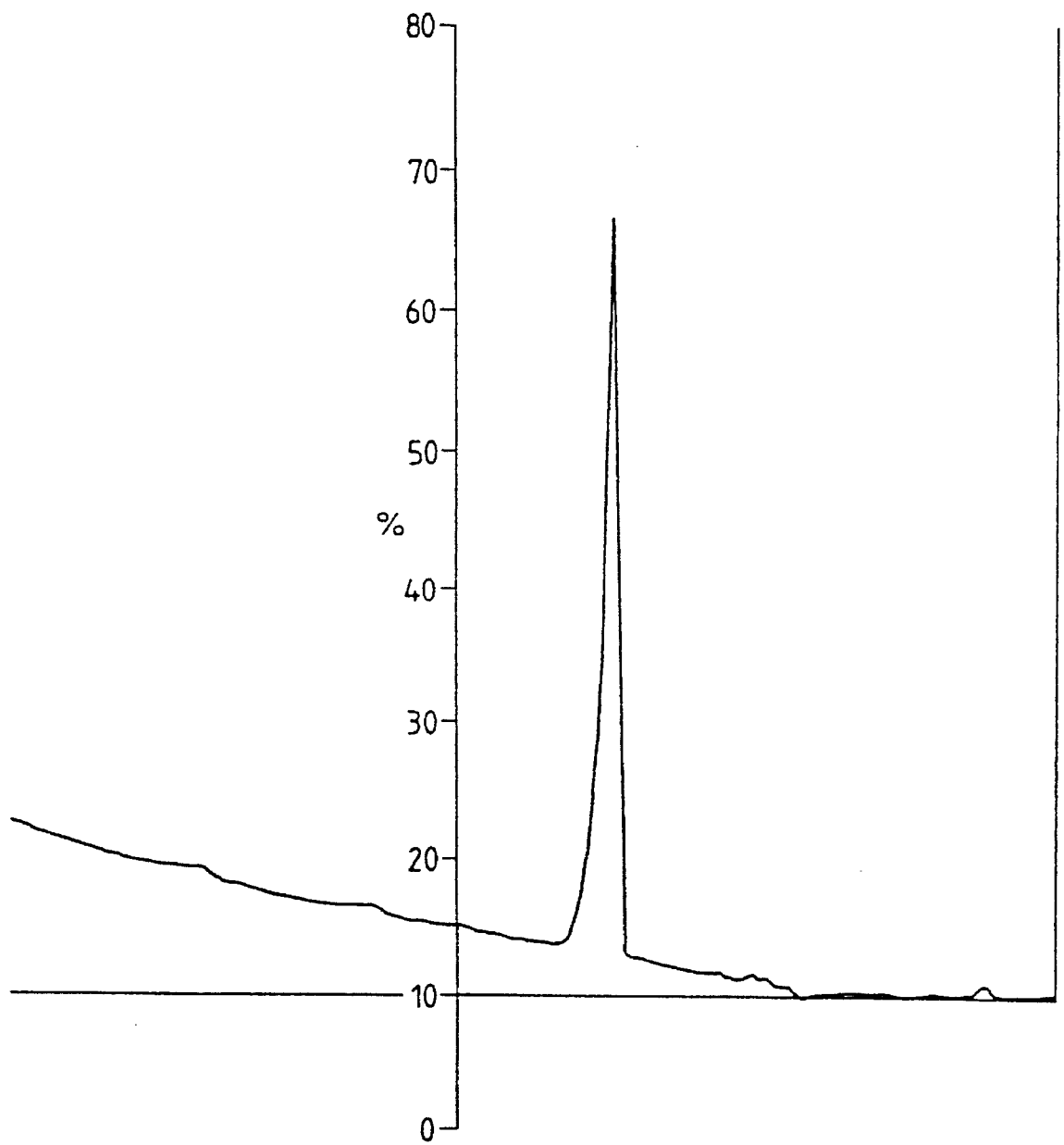
FIG. 3 shows the HPLC trace of purified K(D)PV (Example 5)

The HPLC trace of the purified tripeptide is shown in FIG. 3.

Column: Vydac $C_{18}$ 4.6 mm×25 cm
Solvent: Linear gradient 0–30% B over 30 mins
Flow rate: 1.5 $cm^3$ $min^{-1}$
A=0.1% TFA/$H_2O$
B=0.1% TFA/$CH_3CN$
Detection: UV at 230 nm.

Reference Example: Hyperalgesic Activity of IL-1β

The hyperalgesic activity of IL-1β was investigated by a modified Randall-Sellito rat paw pressure test (Ferreira et al, Eur. J. Pharacol. 53, 39–48, 1978). The IL-1β (and the IL-1α used in Example 7) were human recombinant proteins purchased from Genzyme Ltd and calibrated against Interim Reference Reagents. (These are temporary biological standards from the National Institute for Biological Standards and Control, Potters Bar, GB: for IL-1α 1 unit=10 pg and for IL-1β 1 unit=10 pg).

The development of bilateral hyperalgesia (nociception) after injection of IL-1β into one paw of rats and its attenuation by pretreatment with indomethacin (INDO) was investigated. The IL-1β was given either intraplantar (ipl, injection volume=0.1 ml) or intraperitoneally (ip, injection volume=0.3 ml). Indomethacin was given ipl, 100 µg in 0.1 ml.

Hyperalgesia was evaluated by the application of a constant pressure of 20 mmHg to the hind paws of rats (wistar strain, male, weight 135–170 g) which was discontinued when animals presented a characteristic freezing reaction (reaction time). The intensity of hyperalgesia was quantified as the variation of the reaction time (Δ reaction time, sec) obtained by subtracting the value measured 1,2,3 or 4 h after administration of the hyperalgesic agent from the pre-injection control reaction time (zero time). The experimenter was unaware of the group treatments.

Figure 4:
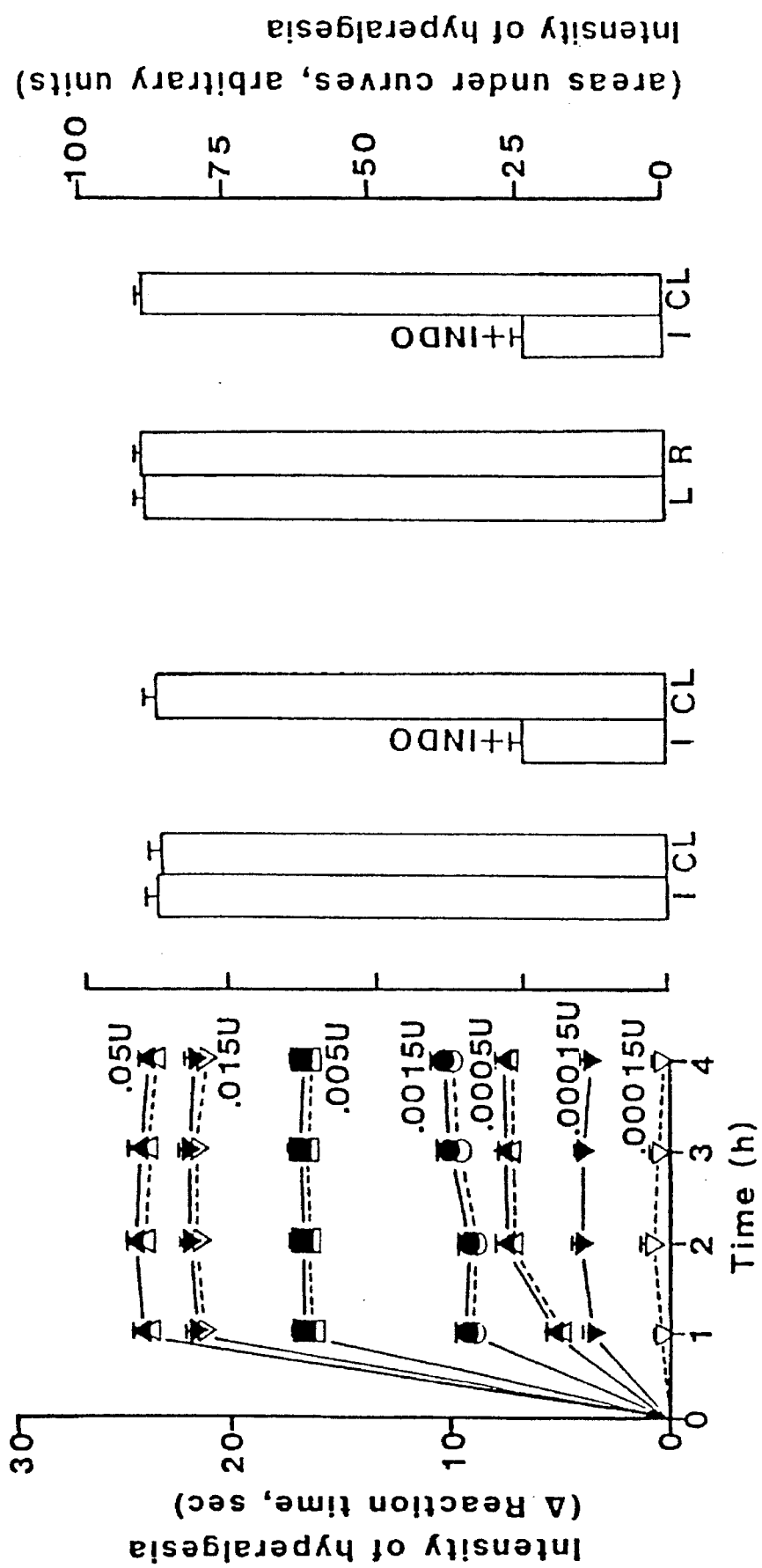

The results are shown in FIG. 4. In Panel A, the Il-1β had been given ipl. The hyperalgesic effect of IL-1β in the injected paws (filled symbols and solid lines) and contralateral paws (open symbols and dotted lines) was determined.

In Panels B and C, the results are presented as "areas under curves" expressed in arbitrary units and calculated from data obtained by measuring the hyperalgesia at intervals of 0, 1, 2, 3 and 4 h after the nociceptive stimulation (Ferreira et al, 1978). The vertical bars are standard errors of the means (s.e.m's) of values obtained in groups of 5 rats.

Panels B and C show the hyperalgesic effect of 0.05 U of IL-1β given ipl and ip respectively and the effect of pretreatment with indomethacin 30 minutes beforehand. The pretreatment markedly attenuated the hyperalgesic response only in treated paws (I). There was no effect in contralateral paws (CL), suggesting that IL-1β causes hyperalgesia by releasing prostaglandin-like substances in the vicinity of nociceptors.

EXAMPLE 6

Effect of peptides on hyperalgesia evoked by IL-1β

The effect of three tripeptides on the hyperalgesia evoked in groups of rats by IL-1β was studied. The three tripeptides were Lys-Pro-Thr (KPT), Lys-D-Pro-Thr (K(D)PT) and a peptide Lys-Asp-Asp (KDD) which is outside the scope of the invention. The results are shown in FIG. 5.

Figure 5:
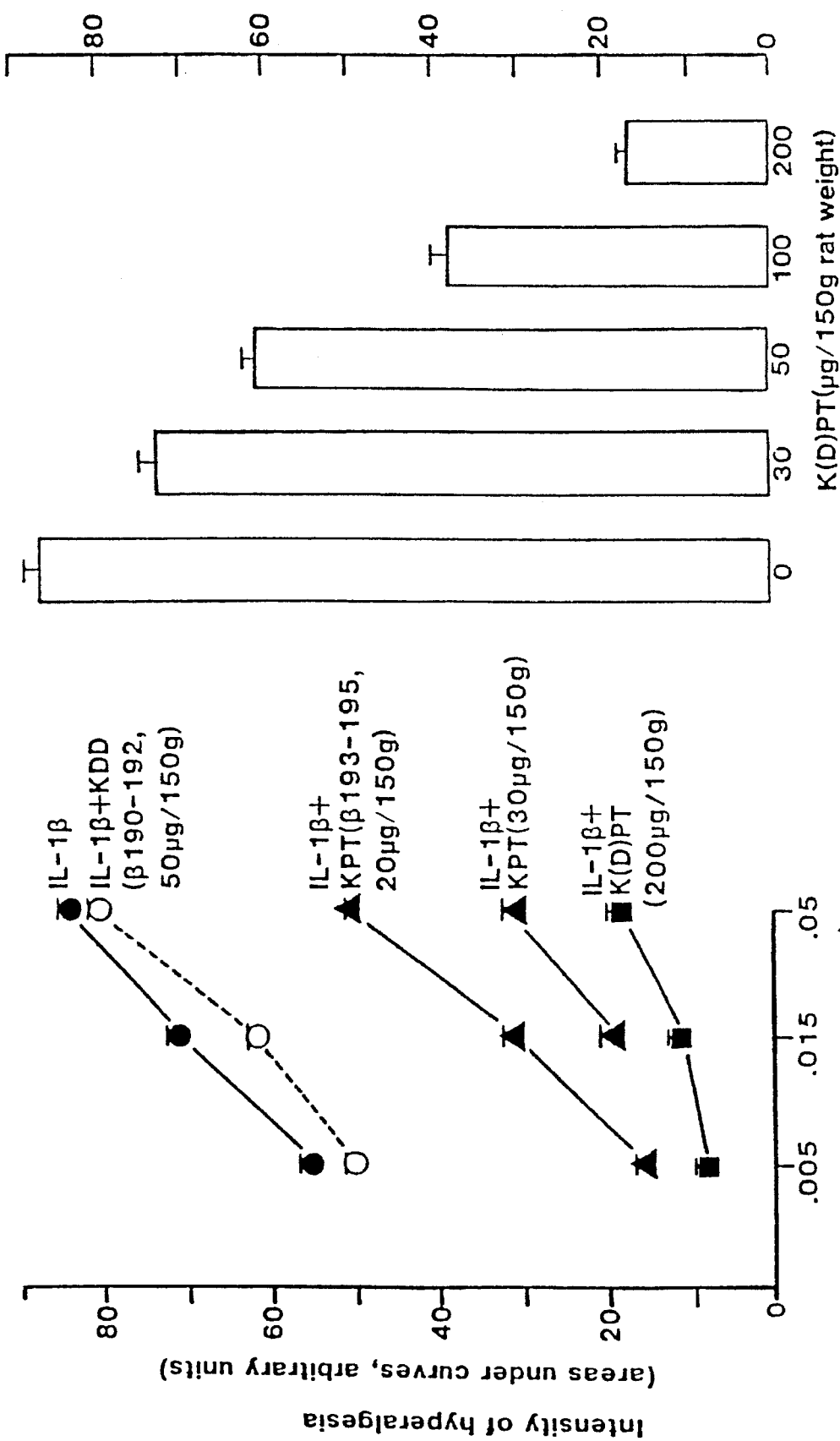

In FIG. 5, Panel A shows the effect of pretreatment with KPT, K(D)PT and KDD, all given subcutaneously (sc), on the hyperalgesic responses the the ip injection, 30 min later, of IL-1β. Panel B shows the dose-dependent antagonism by K(D)PT of the hyperalgesic response to IL-1β (0.05 U/150 g), given ip 30 min later. Each symbol or histogram represents the mean response of 5 animals per treatment group. Vertical bars are s.e.m's.

EXAMPLE 7

Effect of peptide K(D)PT in hyperalgesia evoked by IL-1α and IL-β

The hyperalgesic responses to IL-1α and IL-1β was evaluated in rats. The effect of K(D)PT on those responses was determined. The results are shown in FIG. 6. The data are means ±s.e.m.'s of 5 animals per treatment group. The K(D)PT (200 µg/150 g rat weight) was given sc, 30 min before the ip injection of IL-1.

FIG. 6 shows that inhibition of the bilateral hyperalgesic effect of IL-1β could be overcome by increasing the dose of IL-1β, which is consistent with competitive antagonism. Also from FIG. 6 it can be seen that IL-1β was about 3000 times more potent that IL-1α as a hyperalgesic agent and that IL-1α, which lacks the sequence Lys-Pro-Thr, was only weakly antagonised by K(D)PT.

EXAMPLE 8

Effect of peptide K(D)PT on hyperalgesia evoked by $PGE_2$, carrageenan and IL-1β

Figure 7:
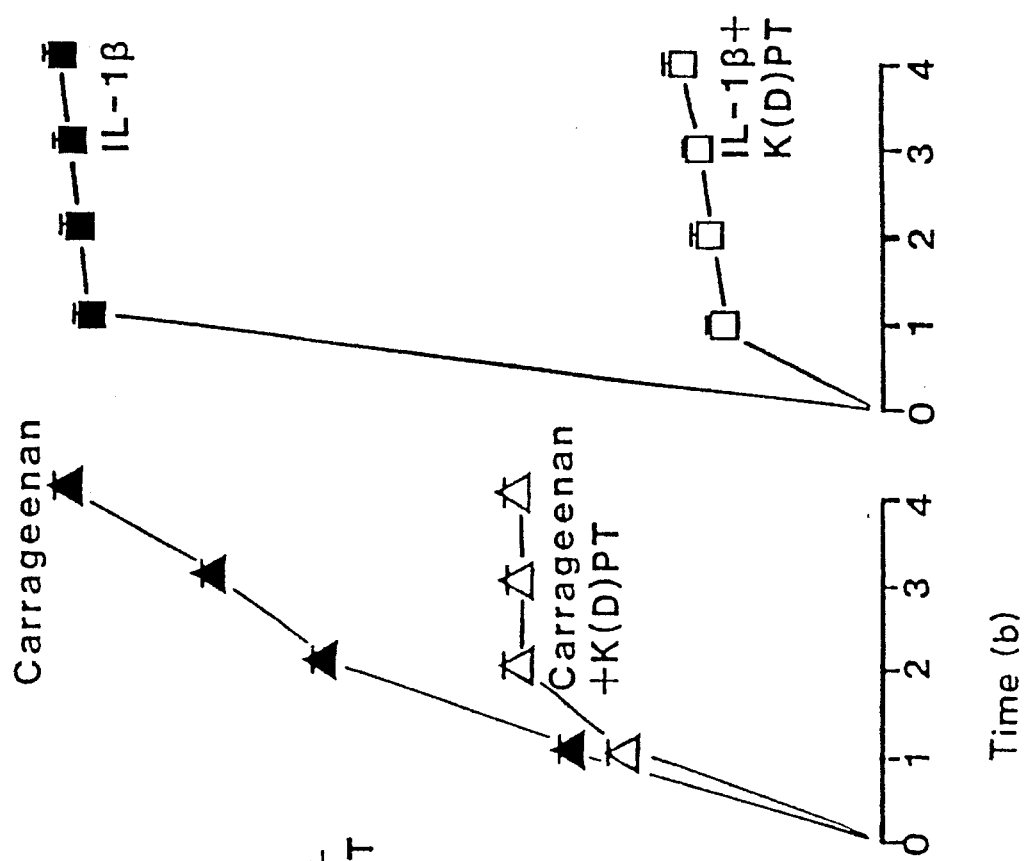

The effect of K(D)PT on hyperalgesia evoked by $PGE_2$, carrageenan and IL-1β was evaluated in rats. The results are shown in FIG. 7. The panels show the temporal development of hyperalgesic responses to A: $PGE_2$ (100 ng/paw), B: carrageenan (100 µg/paw) and C: IL-1β (0.05 U/paw).

K(D)PT (200 µg/150 g) was injected ip, 30 min before the ipl injections. Each symbol represents the mean response of 5 animals per treatment group. Vertical bars are s.e.m.'s.

The oedema that developed after injection of carrageenan was measured, pletismographically (Ferreira, J. Pharm. Pharmacol., 31,648, 1979), 4 h after the challenge. The oedema was not diminished by pretreatment with K(D)PT (data not shown). K(D)PT given two hours after the IL-1β or carrageenan had no effect on the induced hyperalgesia, whereas centrally acting analgesics, eg. morphine and dipyrone, and the peripheral analgesic BW 443C are able to antagonise on-going hyperalgesia. Taken together with the finding that K(D)PT had no effect on $PGE_2$-evoked hyperalgesia, these results indicate that the analgesic effect of K(D)PT was neither central or non-specific.

EXAMPLE 9

Effect of peptide K(D)PT on hyperalgesia evoked by acetic acid and Iloprost

The effect of K(D)PT on the hyperalgesia evoked in groups of 5 mice by acetic acid and Iloprost was determined. Iloprost is a stable analogue of prostacyclin and has the formula:

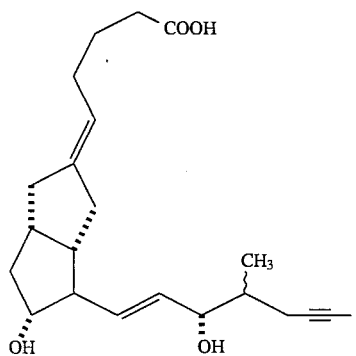

K(D)PT was given sc before the ip injections of 0.6% acetic acid or Iloprost (10 µg/kg) which caused contortions (writhing). The % inhibition of this response after pretreatment with K(D)PT is shown in Table 1:

TABLE 1

| K(D)PT mg/kg | % inhibition of response to acetic acid (0.6%) | % inhibition of response to Iloprost (10 µg/kg) |
|---|---|---|
| 0 | 0 | 0 |
| 0.5 | 11 | 0 |
| 2 | 36 | 27 |
| 8 | 45 | 33 |
| 32 | 41 | 38 |

EXAMPLE 10

Comparison of the effect of peptide K(D)PT and of indomethacin on hyperalgesia evoked by acetic acid and Iloprost Example 9 was repeated with some groups of mice given indomethacin at various doses rather than the peptide K(D)PT. A control group of mice received neither indomethacin nor K(D)PT. The results are shown in Table 2. The data are the total number of contortions measured during 20 minutes after the ip challenge.

TABLE 2

| TREATMENT | | INDOMETHACIN (mg/kg) | | | K(D)PT (mg/kg) | | | |
|---|---|---|---|---|---|---|---|---|
| ip injection | CONTROL | 1.25 | 5.0 | 20.0 | .5 | 2.0 | 8.0 | 32.0 |
| ACETIC ACID.6% 0.1 ml/10 g | 45.3 ± 2.8 (–%) | 34.6 ± 4.1 23.6% | 24.3 ± 5.7 46.3% | 19.3 ± 2.6 57.4% | 38.6 ± 2.0 14.7% | 31.6 ± 2.4 30.2% | 24.2 ± 2.0 46.5% | 25.6 ± 1.5 43.4% |
| ILOPROST 10 µg/kg | 39.4 ± 6.1 (–%) | 36.4 ± 4.3 7.6% | 29.2 ± 2.7 26.0% | 21.3 ± 1.3 46.0% | 34.6 ± 3.7 9.6% | 26.0 ± 2.4 34.0% | 22.4 ± 1.1 43.2% | 23.8 ± 3.1 40.0% |

K(D)PT was therefore effective in reducing contortions induced in mice by the ip injection of acetic acid and of Iloprost. A dose of 8 mg/kg of K(D)PT produced a maximal analgesia (no difference between 8 and 32 mg/kg) of the order of 45% which corresponded to the effect of doses of 5 and 20 mg/kg of indomethacin. However, indomethacin caused gastric lesions in the mice whilst peptide K(D)PT did not. At a dose of 20 mg/kg of indomethacin, gastric erosions were caused in 100% of the mice. No lesions were observed with a dose of 32 mg/kg of K(D)PT.

EXAMPLE 11

K(D)PT is not a centrally-acting morphine-like analgesic

A standard hot plate (55° C.) test was carried out. The results are shown in Table 3. The results are the mean s.e.m. of the reaction time obtaining by subtracting from the reaction time before treatment the values observed 1 hour after the administration of the two drugs. The Table shows that K(D)PT is not morphine-like.

TABLE 3

| saline | Morphine (mg/kg) | | K(D)PT (mg/kg) |
|---|---|---|---|
| sc injection | 3.0 | 9.0 | 32.0 |
| −1.1 ±0.4 | 3.52 ±1.0 | 5.55 ±0.7 | 0.37 sec ±0.4 |

EXAMPLE 12

K(D)PT is not aspirin-like (i.e. an inhibitor of cyclooxygenase)

The effect of K(D)PT and indomethacin on $PGE_2$ release by human blood mononuclear cells (MNC) was investigated. The MNC were isolated from buffy coat residues by density gradient centrifugation (Ficoll-hypaque, Sigma) and resuspended in RPMI 1640 culture medium (Gibco)+2% inactivated foetal calf serum (Imperial Laboratories). Materials were added to the incubation media as shown in Table 4. K(D)PT and indomethacin were added 45 min before IL-1β or endotoxin. The results are shown in Table 4. Values are means of quadruplicates ±s.e.m.'s. $PGE_2$ concentrations were measured by radioimmunoassay (NEN Research Products).

TABLE 4

| Materials added to incubation media | $PGE_2$ release (ng/ml) by MNC (5 × 10⁶ cells/ml) incubated for 4 h with: | | | |
|---|---|---|---|---|
| | Saline control (0.9% w/v) | IL-1α (50 U/ml) | IL-1β (50 U/ml) | E. coli endotoxin[a] (25 pg/ml[b]) |
| Saline control (0.9% w/v) | 0.9 ± 0.1 | 1.8 ± 0.1 | 2.7 ± 0.2 | 3.5 ± 0.2 |
| 0.1% v/v dimethylsulphoxide (control for K(D)PT) | 1.0 ± 0.1 | 1.6 ± 0.1 | 2.2 ± 0.2 | 3.5 ± 0.2 |
| K(D)PT (200 g/ml, 0.58 millimoles/L) | 1.3 ± 0.3 | 2.0 ± 0.2 | 2.8 ± 0.2 | 4.1 ± 0.3 |
| 0.012% v/v ethanol (control for indomethancin) | 1.3 ± 0.2 | 2.0 ± 0.2 | 2.1 ± 0.1 | 3.1 ± 0.2 |
| Indomethacin (2 μg/ml, 5.9 micromoles/L) | 0.03 ± 0.0002 | 0.03 ± 0.0007 | 0.03 ± 0.0005 | 0.03 ± 0.0004 |

[a] E.coli 0113:H10:K(−) endotoxin;
[b] 25 pg/ml = 0.18 IU/ml

K(D)PT had no effect on production of $PGE_2$ by MNC whereas a hundred times lower dose of the potent aspirin-like drug indomethacin abolished $PGE_2$ production by these cells.

EXAMPLE 13

Effect of peptides on hyperalgesia evoked by IL-1β

The effect of the tripeptides Lys-Pro-Val (KPV), Lys-D-Pro-Val (K(D)PV) and Lys-D-Pro-Thr (K(D)PT) on hyperalgesia evoked in rats by IL-1β was studied. The results are given in Table 5 which follows. Treatments were given ip, 1 h before Il-1β, also given ip. There were animals per treatment group.

Delta reaction time was measured 3 h after Il-1β administration.

The Control was Il-1β (0.05U), given ip. The result for the control group was 23.9±0.5 (=100%).

TABLE 5

| TREATMENT PEPTIDE | DELTA REACTION TIME (sec) DOSAGE μg/150 g rat weight | | | |
|---|---|---|---|---|
| | 20 | 50 | 100 | 200 |
| K(D)PT | Not tested | 18.7 ± 0.5 (−21.8%) | 12.8 ± 0.6 (−46.4%) | 6.3 ± 0.4 (−73.6%) |
| KPV | 18.8 ± 0.3 (−21.3%) | 11.3 ± 0.5 (−52.7%) | 7.2 ± 0.6 (−69.9%) | 3.9 ± 0.3 (−83.7%) |
| K(D)PV | 18.2 ± 0.4 (−23.9%) | 8.5 ± 0.6 (−64.4%) | 3.8 ± 0.7 (84.1%) | 2.8 ± 0.6 (−88.3%) |

Example 14

Effect of peptides on hyperalgesia evoked by $PGE_2$

The effect of the tripeptide K(D)PT on hyperalgesia evoked in rats by $PGE_2$ was studied. The results are shown in Table 6 below. Treatments were given ip, 1 h before $PGE_2$ was injected into the paw (ipl). There were 5 animals per treatment group. Delta reaction time was measured 3 h after $pGE_2$ administration. Morphine (0.6 mg/150 g) reduced delta reaction time to 6.1±0.8 sec (−63.7%). The control was $PGE_2$ (100 mg/paw). The results for the control group were 16.8±0.3 (=100%). NT=Not tested.

TABLE 6

| TREATMENT PEPTIDE | DELTA REACTION TIME (sec) DOSE μg/150 g rat weight | | | |
|---|---|---|---|---|
| | 20 | 50 | 100 | 200 |
| K(D)PT | NT | NT | NT | 16.7 ± 0.6 (−0.6%) |
| KPV | 14.9 ± 0.4 (−11.3%) | 13.0 ± 0.3 (−22.6%) | 9.9 ± 0.2 (−41.1%) | 7.8 ± 0.6 (−53.6%) |
| K(D)PV | 14.0 ± 0.4 (−16.7%) | 13.4 ± 0.4 (−20.2%) | 9.0 ± 0.2 (−46 ± 4%) | 6.0 ± 0.3 (−64.3%) |

EXAMPLE 15

Effect of peptidase on hyperalgesia evoked by DbcAMP (control)

The effect of the tripeptides KPV and K(D)PV on hyperalgesia evoked in rats by DbcAMP was studied. The results are given in Table 7 below. Treatments were given ip, 1 h before DbcAMP was injected into the paw (ipl). There were 5 animals per treatment group. Delta reaction times were measured 3 h after DbcAMP. Morphine (0.6 mg/150 g) reduced delta reaction time to 6.2±0.4 sec (−64.0%). The control was DbcAMP (100 μg/paw). The results for the control group were 17.2±6.4 sec (=100%).

TABLE 7

| TREATMENT PEPTIDE | DELTA REACTION TIME 200 μg/150 g rat weight |
|---|---|
| K(D)PT | 17.8 ± 0.6 (+3.5%) |
| KPV | 15.8 ± 0.3 (−8.1%) |
| K(D)PV | 16.0 ± 0.2 (−7.0%) |

EXAMPLE 16

Preparation of D-Lys-Pro-Thr

The tripeptide D-Lys-Pro-Thr was synthesised and purified in accordance with the procedure described in Example 1. Purity was established by amino acid analysis, FAB-MS and HPLC:

| amino acid analysis | calculated | found | |
|---|---|---|---|
| | 1 | 0.97 | Lys |
| | 1 | 1.03 | Pro |
| | 1 | 1.00 | Thr |

FAB-MS: positive ion spectrum gave M+H$^+$ at m/z 345 (molecular weight is 344.415 (344))

HPLC: column: Vydac $C_{18}$ 4.6 mm×25 cm solvent: linear gradient 0–30% B over 30 minutes;

A=0.1% TFA/H$_2$O and B=0.1% TFA/CH$_3$CN; flow rate= 1.5 cm$^3$ min$^{-1}$

The trace obtained is shown in FIG. 8.

EXAMPLE 17

Preparation of Lys-D-Pro

The dipeptide Lys-D-Pro was synthesised and purified in accordance with the procedure described in Example 1. Purity was established by amino acid analysis and HPLC.

| amino acid analysis | calculated | found | |
|---|---|---|---|
| | 1 | 1.04 | Lys |
| | 1 | 0.96 | Pro |

HPLC: column: Vydac $C_{18}$ 4.6 mm×25 cm solvent: linear gradient 0–10% B in 30 minutes;

A=0.1% TFA/H$_2$O and B=0.1% TFA/CH$_3$CN; flow rate= 1.5 ml min$^{-1}$; chart speed=5 mm min$^{-1}$ The trace obtained is shown in FIG. 9.

EXAMPLE 18

Preparation of Lys-D-Pro-Asn

The tripeptide Lys-D-Pro-Asn was synthesised and purified in accordance with the procedure described in Example 1. Purity was established by HPLC under the same conditions as in Example 17, amino acid analysis and FAB-MS.

| amino acid analysis | calculated | found | |
|---|---|---|---|
| | 1 | 1.00 | Lys |
| | 1 | 0.90 | Pro |
| | 1 | 1.03 | Asn |

FAB-MS: positive ion spectrum gave M+H$^+$ at m/z 358 (molecular weight is 357.413).

EXAMPLE 19

Effect of peptides on hyperalgesia evoked by acetic acid

The effect of peptides on the hyperalgesia evoked by acetic acid in groups of mice (LACA, male, 25–35 g, 6≦n≦9) treated with one dose of one of the peptides or with morphine, indomethacin or saline (0.1 ml/10 g) was determined. Drugs were injected intraperitoneally (ip) or were give orally (po), 30 min before ip injection of acetic acid (0.6% v/v, 0.1 ml/10 g). The number of contortions (abdominal constrictions or writhes) was counted in the period between 10 and 20 min after ip challenge with acetic acid by an observer unaware of drug treatment. The median values were calculated and comprise the date given in Tables 8 to 11. The numbers in parenthesis are the % reductions from control values in mice injected with saline control. [1]: morphine 2.5 mg/kg ip; [2]: morphine 1.25 mg/kg ip.

From Tables 8 to 11 it can be seen that the tripeptides K(D)PV (Example 5), (D)KPT (Example 16), KPT (Example 1) and K(D)PT (Examples 2 and 3), given ip at 2–100 mg/kg, all possessed dose-related analgesic activity against hyperalgesia evoked by acetic acid in mice. In this test, 30 mg/kg ip of each peptide appeared to be about as effective as a dose of 1.25 mg/kg ip morphine or 5 mg/kg indomethacin (ip) (Tables 8 and 10). Further, the four tripeptides possessed analgesic activity when given orally (po) (Table 11). Also the dipeptide K(D)P was an effective analgesic whether given ip (Table 9) or po (Table 11).

TABLE 8

| | Dose drug of (mg/kg, ip) | | | |
|---|---|---|---|---|
| Drug | 2 | 10 | 30 | 100 |
| K(D)PV | 19(−33%) | 17(−38%) | 15.5(−45%) | 7(−74%) |
| (D)KPT | 20.5(−28%) | 24.5(−11%) | 14(−50%) | 9(−66%) |
| KPT | 19(−33%) | 19(−31%) | 14(−50%) | 8(−70%) |
| K(D)PT | 24(−16%) | 22(−20%) | 15(−46%) | 13.5(−49%) |
| Morphine | 8(−72%)[1] | 8(−71%)[1] | 14.5(−48%)[2] | 8(−71%)[1] |

TABLE 9

| Drug | Dose of drug (mg/kg, ip) | | |
|---|---|---|---|
| | 5 | 10 | 20 |
| K(D)P | | 14.5(−45%) | 6(−77%) |
| K(D)P | 11(−58%) | 6(−77%) | |

TABLE 10

| Drug | Dose of drug (mg/kg, ip) | | |
|---|---|---|---|
| | 2.5 | 5 | 10 |
| Indomethacin | 16.5(−37%) | 10(−61.5%) | 10(−61.5%) |

TABLE 11

| Drug | Dose of drug (mg/kg, po) | | | |
|---|---|---|---|---|
| | 5 | 10 | 20 | 100 |
| K(D)PV | | | | 13(−52%) |
| (D)KPT | | | | 11(−59%) |
| KPT | | | | 9(−67%) |
| K(D)PT | | | | 8(−70%) |
| K(D)P | 19(−10%) | 13.5(−36%) | 14(−38%) | |

We claim:

1. A compound selected from the group consisting of
   (a) a peptide of formula (I):

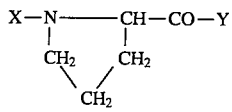

wherein X is selected from the group consisting of
H$_2$N—(CH$_2$)$_4$—CH(NH$_2$)—C(=O)— and
H$_2$N—C(=NH)—NH—(CH$_2$)$_3$—CH(NH$_2$)—C(=O)—
and Y is a naturally occurring amino acid residue;
   (b) the C-terminal amide thereof, and
   (c) a pharmaceutically acceptable salt of the said peptide or amide; with the provisos that
       (i) the proline residue is D-Pro, and
       (ii) the peptide is not selected from the group consisting of Arg-D-Pro-Pro, Arg-D-Pro-Lys, D-Lys-D-Pro-D-Arg, Lys-D-Pro-Val and D-Lys-D-Pro-D-Val.

2. A compound selected from the group consisting of:
   (a) a peptide of formula (I):

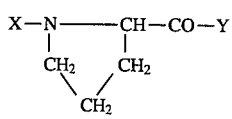

wherein X is selected from the group consisting:
H$_2$N—(CH$_2$)$_4$—CH(NH$_2$)—C(=O)— and
H$_2$N—C(=NH)—NH—(CH$_2$)$_3$—CH(NH$_2$)—C(=O)—
and Y is selected from the group consisting of a threonine, valine, alanine, serine, leucine, isoleucine, aspartic acid and asparagine residue,
   (b) the C-terminal amide thereof, and
   (c) a pharmaceutically acceptable salt of the said peptide or amide; with the provisos that
       (i) the proline residue is D-Pro; and
       (ii) the peptide is not selected from the group consisting of Lys-D-Pro-Val and D-Lys-D-Pro-D-Val.

3. A compound according to claim 1, 2 or 3 wherein the peptide is selected from the group consisting of Lys-D-Pro-Asn, Arg-D-Pro-Val, D-Arg-D-Pro-Val, Arg-D-Pro-Thr, and D-Arg-D-Pro-Thr.

4. A pharmaceutical composition comprising a pharmaceutically effective amount of a compound as defined in claim 1, 2 or 3 and a pharmaceutically acceptable carrier or diluent.

5. A pharmaceutical composition according to claim 4 wherein the peptide is selected from the group consisting of Lys-D-Pro-Asn, Arg-D-Pro-Val, D-Arg-D-Pro-Val, Arg-D-Pro-Thr and D-Arg-D-Pro-D-Thr.

6. A compound selected from the group consisting of
   (a) a peptide of formula (A)

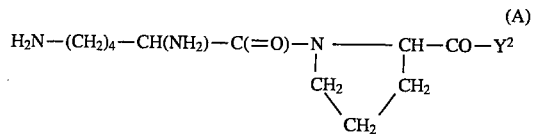

wherein Y$^2$ is a threonine, alanine, serine, leucine, isoleucine, aspartic acid or asparagine residue;
   (b) a peptide of formula (B):

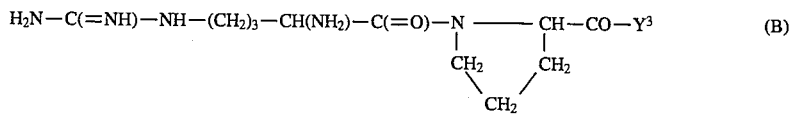

wherein Y$^2$ is a threonine, valine, alanine, serine, leucine, isoleucine, aspartic acid or asparagine residue;
   (c) the C-terminal amide of a said peptide under (a) or (b) above; and
   (d) a pharmaceutically acceptable salt of a said peptide under (a), (b) or (c) above;
with the proviso that the proline residue in formula (A) and formula (B) is D-Pro.

7. A pharmaceutical composition comprising a pharmaceutically effective amount of a compound as defined in claim 6 and a pharmaceutically acceptable carrier or diluent.

* * * * *